(12) United States Patent
Arbuckle et al.

(10) Patent No.: US 6,716,729 B2
(45) Date of Patent: Apr. 6, 2004

(54) STABLE BISPHENOLIC COMPOSITIONS

(75) Inventors: Stephen Wayne Arbuckle, Louisville, KY (US); Vinay Malhotra, Louisville, KY (US); John George Juras, Jr., Georgetown, IN (US)

(73) Assignee: Borden Chemical, Inc., Columbus, OH (US)

( * ) Notice: Subject to any disclaimer, the term of this patent is extended or adjusted under 35 U.S.C. 154(b) by 12 days.

(21) Appl. No.: 10/070,623

(22) PCT Filed: Dec. 19, 2000

(86) PCT No.: PCT/US00/34542

§ 371 (c)(1),
(2), (4) Date: Mar. 4, 2002

(87) PCT Pub. No.: WO01/46101

PCT Pub. Date: Jun. 28, 2001

(65) Prior Publication Data

US 2003/0094594 A1 May 22, 2003

Related U.S. Application Data

(60) Provisional application No. 60/171,356, filed on Dec. 22, 1999.

(51) Int. Cl.$^7$ ......................... B32B 27/42; C08G 14/04; C08G 8/26; C08L 61/14; C09K 3/00
(52) U.S. Cl. ............. 438/531; 252/182.24; 252/182.25; 427/411; 528/155; 568/724
(58) Field of Search ....................... 252/182.24, 182.25; 427/411; 428/531; 528/155; 568/724

(56) References Cited

U.S. PATENT DOCUMENTS

| | | |
|---|---|---|
| 2,858,342 A | 10/1958 | Bender et al. |
| 3,048,508 A | 8/1962 | Boiney |
| 3,277,183 A | 10/1966 | Heller et al. |
| RE26,881 E | 5/1970 | Kreibich et al. |
| 3,594,268 A | 7/1971 | Dahms et al. |
| 3,920,573 A | 11/1975 | Vegter et al. |
| 3,972,950 A | 8/1976 | Kwantes |
| 4,107,127 A | 8/1978 | Shea |
| 4,124,554 A | 11/1978 | Fry |
| 4,150,194 A | 4/1979 | Watts et al. ................. 428/531 |
| 4,179,429 A | 12/1979 | Hanauye et al. |
| 4,240,968 A | 12/1980 | Quinn et al. |
| 4,242,527 A | 12/1980 | Mark et al. .................. 568/724 |
| 4,294,993 A | 10/1981 | Li ............................... 568/724 |
| 4,318,840 A | 3/1982 | Doyle et al. ................. 523/144 |
| 4,320,042 A | 3/1982 | Anderson et al. ........... 523/144 |
| 4,337,334 A | 6/1982 | Shimizu et al. |
| 4,408,087 A | 10/1983 | Li ............................... 568/724 |
| 4,413,113 A | 11/1983 | Gelling et al. .............. 528/165 |
| 4,514,462 A | 4/1985 | Brooker ...................... 428/285 |
| 4,656,239 A | 4/1987 | Waitkus et al. ............. 528/140 |
| 4,861,919 A | 8/1989 | Robbins et al. ............. 568/724 |
| 5,275,758 A | 1/1994 | Wulff et al. |
| 5,300,699 A | 4/1994 | Furukawa et al. .......... 568/724 |
| 5,434,316 A | 7/1995 | Kissinger .................... 568/724 |
| 5,478,908 A | 12/1995 | Hesse et al. ................. 528/155 |
| 5,552,509 A | 9/1996 | Takashima et al. ......... 528/129 |
| 5,637,658 A | 6/1997 | Teodorczyk ................. 525/480 |
| 5,646,219 A | 7/1997 | Teodorczyk ................. 525/524 |
| 5,696,295 A | 12/1997 | Wulff et al. ................. 568/724 |
| 5,756,599 A | 5/1998 | Teodorczyk ................. 525/491 |
| 5,847,058 A | 12/1998 | Teodorczyk ................. 525/480 |
| 6,307,111 B1 * | 10/2001 | Fennhoff et al. ........ 568/724 X |

FOREIGN PATENT DOCUMENTS

| | | |
|---|---|---|
| JP | 60261639 A | 12/1985 |

\* cited by examiner

*Primary Examiner*—Richard D. Lovering
(74) *Attorney, Agent, or Firm*—Cantor Colburn LLP

(57) ABSTRACT

There is provided a stable single-phase composition of bisphenolic stillbottoms and methods for making such compositions. There is also provided a resole and a novolac composition that includes in the manufacture of the resins the use of a stable solution of bisphenolic stillbottoms. Methods for making the resins are also provided. There is further provided a low molecular weight phenolic resin useful in the manufacture of paper laminates, such that the resin exhibits improved paper saturation and reduced phenol emissions during treating when compared to the prior art. There is also provided a laminate composition that results in a paper laminate that exhibits improved flexibility when compared to the prior art.

64 Claims, No Drawings

STABLE BISPHENOLIC COMPOSITIONS

This application claims the benefit of provisional application No. 60/171,356, filed Dec. 22, 1999.

FIELD OF THE INVENTION

This invention relates to a method of manufacturing a stable solution containing bisphenolic stillbottoms. This invention also relates to phenolic compositions that are manufactured using solutions of bisphenolic stillbottoms. This invention further relates to phenolic compositions that are useful in the manufacture of laminates and paper products.

BACKGROUND OF THE INVENTION

Bisphenol A stillbottoms, as one example of bisphenolic stillbottoms known in the art, are produced by dehydrocondensing phenol and acetone in the presence of a strong acid catalyst. When bisphenol A is separated from the reaction mixture by distillation, for example, or by other purification methods, there is a material remaining that has been generally described in the art as a bisphenol stillbottom. Consistent with the use of the term in the art, hereinafter, the term bisphenol stillbottoms refers to that material separated during the preparation of bisphenol that is not purified bisphenol. Thus, bisphenol A stillbottoms may contain some bisphenol A. The bisphenol A stillbottom typically contains, in predominant proportions, other phenol-acetone reaction products. Dihydroxydiphenylpropane isomers and chromane compounds are typically present in lesser amounts.

The reuse of bisphenolic stillbottoms is generally quite limited. Bisphenolic stillbottoms are a solid at room temperature and typically must be kept in a molten state, or processed into a small particle such as a flake or powder, if the stillbottoms are to be further used in most manufacturing processes. Molten stillbottoms are subject to degrading oxidation Therefore, the chemical composition of the stillbottoms will change as function of the length of storage time in the molten state. As a result of this changing chemical composition, products made using molten stillbottoms may have unpredictable properties. The processing of stillbottoms into an intermediate form, such as a flake or powder, adds significant cost to products made using this intermediate form and a flake or powder may sinter. Therefore, typically, bisphenolic stillbottoms are incinerated for disposal.

The use of bisphenolic stillbottoms in phenolic resin compositions has until now been limited. Not surprisingly, because phenolic resins are typically condensed from aqueous solutions, the insolubility of bisphenoic stillbottoms generally makes their use prone to problems. In one prior art process, for example, bisphenol A stillbottoms must be further refined before they are useable in the synthesis of a novolac resin. In this process, bisphenol A stillbottom are further processed, at extreme temperatures, reduced pressures and in the presence of an alkaline catalyst, to recover phenol and isopropenyl phenol. A residue remains after such processing and this residue is said to be useful in the manufacture of novolac resins.

The use of bisphenols in phenolic resin synthesis in the prior art is surprisingly limited. As described above with respect to bisphenol stillbottoms, the relative insolubility of bisphenolic compounds generally makes their use prone to problems. For example, in one prior art composition, alkylidenepolyphenols, together with a trifunctional phenol and formaldehyde, are used in the synthesis of resoles. However, as the prior art provides, the timing of the addition of the alkylidenepolyphenol is critical. The alkylidenepolyphenol can be added neither at the start of the synthesis nor near the end of the synthesis, but must be added at some mid-point in the reaction sequence. One prior art process describes a resin that is the reaction of product of formaldehyde and bisphenol A. However, as the prior art teaches, it is essential to maintain a very narrow mole ratio of formaldehyde to bisphenol A. Resins of this type have limited application as leveling compounds or metal coating compounds.

The preparation of aqueous solutions of bisphenolic stillbottoms, let alone the use of these aqueous solutions in the manufacture of resins, until now has been unknown in the art. It has been generally concluded in the prior art that bisphenolic stillbottoms do not form stable aqueous solutions. It has been taught in the prior art that bisphenol A, for example, forms a two-phase system with hot water. It is known that molten bisphenol A forms a two-phase system with water at temperatures even as high as 85° C. to 100° C. In fact, it has long been known in the art that water washing of phenolic mixtures is one means to recover a relatively pure phenol product. The water will dissolve inorganic salts and acid impurities, while the phenolic product readily separates from the aqueous solution.

The development of methods that would allow reuse of bisphenolic stillbottoms have understandably been the object of few prior art attempts. One prior art process provides an aqueous suspension of ultrafine bisphenol particles. Strongly alkaline compounds are used in the preparation of such a suspension. This suspension is used in the preparation of polycarbonates. Yet another prior art process uses strongly alkaline compounds, such as sodium hydroxide, to provide for the dissolution of bisphenol A in hot water. In this prior art process, purified bisphenol A may be recovered from a bisphenolic mixture. Fractions of the bisphenolic mixture will dissolve in the hot water in increasing amounts as the amount of sodium hydroxide is increased. Purified insoluble bisphenol A is recovered by separation from the liquid portion that contains the soluble fractions. Still another prior art process employs a co-solvent, such as an alcohol, to provide for the dissolution of diphenols in water. In this prior art process bisphenol A is said to dissolve in a water/alcohol solution that has been heated to reflux. This process is said to be useful in the purification of bisphenol A.

Each of the prior art processes has disadvantages. A heterogeneous two-phase system of bisphenolic stillbottoms and water is an impractical composition both for the storage of bisphenolic stillbottoms and the use of the stillbottoms in the synthesis of resins. Likewise, the use of strongly alkaline materials or co-solvents adulterates the bisphenolic stillbottoms thus limiting the further use of the modified stillbottoms. The use of molten bisphenolic stillbottoms can result in degradation of the bisphenolic stillbottoms thus affecting the properties of resins made using such stillbottoms. Pre-processing the bisphenolic stillbottoms into a flake or powder is costly. Furthermore, flakes or powders must be re-dissolved during the synthesis of a resin in order for the flake or resin to participate in the synthesis. The re-dissolution presents yet an additional energy requirement. Purification of the bisphenolic stillbottoms to another form is an energy intensive process that changes the chemical composition of the bisphenolic stillbottoms, thus further limiting the utility of the modified form.

It would therefore be advantageous to have a stable aqueous solution of bisphenolic stillbottoms thus obviating the need to store bisphenolic stillbottoms in a molten state or to further process bisphenolic stillbottoms into a flake or powder form. It would also be an advantage to have a phenolic resin composition that included in the manufacture of the phenolic resin the use of a stable aqueous solution of bisphenolic stillbottoms. It would be a further advantage to have a process for using bisphenolic stillbottoms in the synthesis of phenolic resins that did not require refinement of the bisphenolic stillbottoms into another chemical form.

The preparation of laminates and resin-impregnated papers using phenolic resins is also known in the art. The resins used in such preparations range from low molecular weight resins having a high tolerance for water to high molecular weight resins having a low tolerance for water.

The preparation of laminates and resin saturated papers using phenolic resins based on the prior art has attendant disadvantages. Low molecular weight resins are typically prepared by using a high phenol to formaldehyde ratio, or, in the alternative, a low formaldehyde to phenol ratio. Such resins typically contain a high free phenol content. These resins, accordingly, exhibit high emissions when subjected to the elevated temperatures realized in the manufacture of laminates.

It would therefore be an advantage to have a low cost process for producing low molecular weight resins that also contain low amounts of residual free phenol. It would be a further advantage to have a product of such a process.

SUMMARY OF THE INVENTION

The present invention provides a stable aqueous solution of bisphenolic stillbottoms. The present invention also provides a resole composition that includes in the manufacture of the resin the use of a stable aqueous solution of bisphenolic stillbottoms. The present invention further provides a process for using bisphenolic stillbottoms in the synthesis of phenolic resins that does not require refinement of the bisphenolic stillbottom into another chemical form.

The present invention provides a low molecular weight phenolic resin that exhibits improved paper saturation and reduced phenol emissions during treating when compared to the prior art. The present invention also provides a method for making low molecular weight phenolic resins that provide improved paper saturation and reduced phenol emissions during treating when compared to the prior art.

The present invention further provides a resin, and a method for making such a resin, that results in a paper laminate that can provide improved flexibility when compared to the prior art.

DETAILED DESCRIPTION OF THE INVENTION

According to one embodiment of the present invention, a single-phase composition of bisphenolic stillbottoms is prepared by mixing water and bisphenolic stillbottoms together under controlled conditions. Surprisingly, it has been determined that when water is mixed with molten bisphenolic stillbottoms, under reflux conditions a stable composition results. Such a composition is a single-phase solution at temperatures as low as 75° C., and a single-phase composition that is a semi-solid ranging from a wax-like to a tar-like consistency at room temperature. The single-phase semi-solid can then be reheated to form a single phase liquid.

The preparation of commercial bisphenolic compounds typically involves a distillation step whereby a purified bisphenolic compound is recovered and a residual bisphenolic stillbottom is separated from the recovered product. The bisphenolic stillbottom may also be described as a distillation residue. As is known in the art, the bisphenolic stillbottom exhibits different chemical properties, including reactivity, as compared to the remainder of the feedstock representing the purified products. Bisphenolic stillbottoms useful in the process of the present invention may include bisphenol A stillbottoms. It is generally known in the art that bisphenol A has a purity of at least 98%, on a weight basis and that bisphenol A stillbottoms are of a lesser purity. As noted above, it is also known in the art that bisphenolic stillbottoms exhibit different chemical properties, including reactivity, than bisphenol A, for example.

Bisphenol A stillbottoms are commercially available. One source for such stillbottoms is General Electric Company, Plastics Group, Schenectady, N.Y., under the trade name V-390 PHENOLIC EXTENDER ("V-390"). V-390 is a mixture of products produced during the manufacture of bisphenol A. V-390 is also known under the synonyms and trade name: BPA tar, BPA isomers, and LE 390 PHENOLIC EXTENDER. V-390 has a melting point range of from about 62° C. to about 110° C. (about 144° F. to about 230° F.).

An alternate source for Bisphenol A stillbottoms is Aristech Chemical Corporation, Pittsburgh, Pa. under the product name BPA HEAVIES. BPA HEAVIES is a mixture of Bisphenol A, o,p-Bisphenol A isomers, and phenol. BPA HEAVIES is also known under the synonyms: 4,4'-Isopropylidenediphenol, and Bisphenol A bottoms. BPA HEAVIES begin to melt at about 62° C. (about 144° F.).

Table 1, provided below, characterizes a typical bisphenolic stillbottom composition the composition of the present invention.

TABLE 1

| Component | Estimated Concentration |
| --- | --- |
| p,p-Bisphenol A | 10%–84% |
| o,p-Bisphenol A | 0%–30% |
| Trisphenol | 10%–25% |
| Chroman-I | 0%–3% |
| Phenol | 0%–25% |
| Other Phenol-Acetone Reaction Products | 45%–75% |

The percentages listed in Table 1 are on a weight-per-weight (w/w) basis calculated on the total weight of the bisphenolic stillbottom. It is understood that the component amounts will add up to 100 percent. It should also be evident from the data of table 1, that the bisphenolic stillbottoms of the present invention may contain substantially non-bisphenol A components.

In contrast to the biphenolic stillbottoms of the present invention, bisphenol A melts at 150–155° C. Thus, it can be seen that the composition of bisphenolic stillbottoms, as used herein, is significantly different from the purified bisphenol product from which the bisphenolic stillbottom is separated.

The present invention provides a composition that is substantially lower in cost than bisphenol A. Because the composition of the present invention is a stable, single-phase, composition, it is readily used in the synthesis of resins, in place of bisphenol A, as illustrated by the following examples.

Stable Aqueous Solutions of Bisphenol Stillbottoms

In one embodiment, the bisphenolic stillbottoms are first brought to a molten state. This is accomplished in a vessel to which heat may be applied. Once the bisphenolic stillbottoms are in a molten state water is then added to the vessel containing the molten bisphenolic stillbottoms. The weight of water added to the vessel is from about 1% to about 20% based on the combined weight of water and bisphenolic stillbottoms. Because the temperature of the molten bisphenolic stillbottoms may be near or above 100° C., the atmospheric boiling point of water, it is preferred that the vessel containing the molten stillbottoms be so equipped to reflux the water vapor that may evolve from the vessel.

The water and the molten bisphenolic stillbottoms are then mixed, for about 30 minutes to about 120 minutes, until a single-phase solution is formed.

In a preferred embodiment, the bisphenolic stillbottoms are heated to about 110° C. and water is slowly added, under mixing, over about 15 to 30 minutes. The temperature of the resulting solution is allowed to drop to about 80 to 90° C.

A typical mixing process is described as follows. Components, including the bisphenolic stillbottoms and water, are introduced into a 1 liter four-necked round-bottom flask. The flask is fitted with means to stir the flask contents, means to monitor the temperature of the flask contents, and means to reflux volatile components and products. Reflux is typically afforded by use of a reflux condenser fitted to one opening of the four-necked flask. The condenser is typically cooled using water. Components are pre-weighed before addition to the four-necked flask. The flask contents are heated by an electric heating mantle that is controlled by a rheostat, or by use of a steam table so that specific temperatures may be reached and maintained. Other arrangements will be known to those skilled in the art.

Different diluents have been studied for use in preparing solutions of bisphenolic stillbottoms. Table 2, below, provides data on experiments conducted to determine the compatibility of such diluents. Also included is stability information in terms of the temperature and amount of time over which the solutions were held.

TABLE 2

A Comparison Of Different Diluents for Bisphenolic Stillbottoms

| Diluent | Water | Acetone/Water | Acetone | Acetone |
|---|---|---|---|---|
| Compatibility | Good | Good | Good | Good |
| Weight of Diluent | 10 | 20/10 | 26 | 20 |
| Hold temperature ° C. | 80 | 25 | 25 | 32 |
| Hold time, days | 6 | 6 | >11 | >7 |

In a further study of the compatibility of bisphenolic stillbottoms with various solvents, the data of table 3, below, was collected. In these tests, the bisphenolic stillbottom was heated to about 90 to 110° C. and the diluent was then slowly added, under mixing, over a 5 to 10 minute period of time. Mixing was continued for one hour and the solutions were allowed to cool to room temperature. The number of phases exhibited were observed both at the elevated temperatures and at room temperature.

TABLE 3

A Comparison Of Different Diluents For Bisphenolic Stillbottoms

| | Amount, grams | | | | | | | | |
|---|---|---|---|---|---|---|---|---|---|
| Component: | a | b | c | d | e | f | g | h | i |
| V-390 | 450 | | 450 | | 450 | | 450 | | |
| BPA HEAVIES | | 450 | | 450 | | 450 | | 450 | 450 |
| Phenol | 50 | 50 | | | | | | | |
| MEK[1] | | | 50 | 50 | | | | | |
| IPA[2] | | | | | 50 | 50 | | | |
| Toluene | | | | | | | 50 | 50 | |
| Water | | | | | | | | | 50 |

[1]MEK is methylethylketone
[2]IPA is isopropyl alcohol

All of the solutions studied appeared homogeneous under mixing. Solutions a, c, e, g, and i exhibited homogeneity at both the elevated temperatures (90° C.–100° C.) and at room temperature. Solutions b, d, f, and h showed exhibited homogeneity at the elevated temperatures but showed separation into two phases upon standing and cooling to room temperature.

Certain analytical tests may be employed to characterize the stable compositions of the present invention. These tests are described below.

Cone and Plate Viscosity Determination

Aqueous solutions of bisphenolic stillbottoms were tested for viscosity. Viscosity was determined using the well known cone and plate viscosity method. The cone and plate viscosity is a high shear viscosity that may be measured on a viscometer such as the Brookfield cone and plate viscometer, model 2000H. The Cone and Plate viscometer provides viscosity measurements of small samples utilizing a thermostatically controlled fixed flat plate and a rotating cone. Typically, values measured by the viscometer are converted into centipoise. The cone and plate viscosity results reported below were made at a temperature of 75° C.

Water Content Determination

The water content of the stable aqueous solutions of the present invention were determined using the standard test method for water by the well known Karl-Fischer titration. This method uses Karl-Fischer reagent which is suitable for determining free water and water of hydration in most solid or liquid organic compositions and for a wide range of concentrations (i.e. from a parts per million order of concentration to pure water). This method is also known under the American Standard for Testing Materials method ASTM E 203-86.

The following examples serve to illustrate one embodiment of the present invention.

Stable Solution Preparation

EXAMPLE 1

A 90% aqueous solution of bisphenolic stillbottoms, based on the total solution weight, was prepared as follows. In this example, the atmosphere in the flask was air, however, other atmospheres, such as nitrogen, may be used. To a flask fitted with a means for mixing and a means for reflux as described above, PHENOLIC EXTENDER V-390 ("V-390") was charged. The V-390 was heated from ambient room temperature to 125° C. (257° F.) over a period of 55 minutes, under mixing. At a temperature of 95–125° C. (203–257° F.) V-390 is molten. Although not considered critical to the methods of the present invention, the molten V-390 was mixed for 5 minutes. After mixing the molten V-390 for five minutes, water was added to the flask in an amount that was 10%, on a weight basis, of the combined weight of the V-390 and the water. The temperature of the water at the time of addition was nominally 25° C. (77° F.) and the water was not heated prior to adding it to the flask, although this is not considered a controlling variable. Mixing was maintained during and after the addition of the water. The water immediately began to boil and the temperature of the flask contents rapidly dropped to 100° C. (212° F.). With mixing, and during the first 20 minutes following the addition of the water, the V-390 and the water maintained separate phases. After about 60 minutes, the temperature of the flask contents had decreased to about 95° C. (203° F.), under reflux, and the flask contents now appeared clear and homogeneous.

The now homogeneous solution in the flask was maintained at 95° C. (203° F.) under reflux and mixing for a period of days. Periodically, samples of the homogeneous solution were taken and tests for viscosity, color, and water content were performed on the samples. Table 4 below provides the results of the testing.

TABLE 4

| Elapsed Time At 95° C. (days) | Number of Phases | Water Content (%) | Viscosity (centipoise) |
| --- | --- | --- | --- |
| 0 | | 10.0[1] | 530 |
| 3 | 1 | | 530 |
| 7[2] | 1 | | |
| 13 | 1 | | |
| 21 | 1 | | 800 |
| 23 | 1 | | |
| 29 | 1 | 8.3 | 800 |

[1]Calculated based on initial water charge.
[2]This sample showed the presence of a minor amount of sediment, but otherwise the sample was a single phase. The amount of sediment was not considered significant and therefore the source of the sediment was not determined.

In performing the method of Example 1, it was also observed that water can be added to the stable aqueous solution in order to adjust the viscosity while still maintaining a single phase system. To a sample of the solution of example 1 that had been maintained for 29 days, water was added to adjust the viscosity to 540 centipoise and the water content to 9.2%. The change in water content over time, under the storage conditions described above, is believed to be due to normal losses due to inefficiencies in the reflux process.

Programmed Addition of Water

EXAMPLE 2

It has been determined that water may be metered into molten bisphenolic stillbottoms, in a programmed manner, to make the stable aqueous solutions of the present invention. In this example water in an amount equal to 10% of the combined weight of water and bisphenolic stillbottom was added to molten V-390. In this example, a flask fitted with a means for mixing and a means for determining temperature was used. An atmosphere of air was maintained in the flask. Initially, V-390 was charged to a flask and brought to a temperature of 115° C. (239° F.) and allowed to melt under mixing. Although not considered critical to the methods of the present invention, the V-390 was allowed to mix for about 15 minutes. Water was then added in the amount described above over a 38 minute period under reflux. At the end of the 38 minute period the temperature of the flask contents at decreased to about 100° C. (212° F.). At the end of 38 minute period of water addition, the flask contents were mixed for an additional 47 minutes at 100° C. (212° F.). It was observed that by using the above-described programmed addition no cold gelling of the V-390 occurred upon addition of the water and there was no flooding of the reflux condenser. Inefficiencies in the operation of the condenser can explain loss of water during the mixing of water and bisphenolic stillbottoms at reflux temperatures.

The advantage of this approach is the ease of transfer, addition and dissolution during resin manufacture.

Phenolic Resins Containing Bisphenolic Stillbottoms

In yet another embodiment of the invention, improvements are made in phenolic resins. Bisphenolic stillbottoms may be used to produce phenolic resins useful in the making of laminates and resin impregnated papers. Like the bisphenolic stillbottoms, the stable aqueous solutions of the present invention may also be used in the synthesis of resoles and novolacs. Conventional resole and novolac preparation is further described below and in *Phenolic Resins, Chemistry, Applications and Performance*. (A. Knop and L. A. Pilato, Springer-Verlag (1985)).

Resole Synthesis

The formation of a resole occurs under generally known conditions. The reaction is carried out at a molar ratio of phenolic compound to aldehyde of 1:0.2 to about 1:5. Catalysts typically employed include sodium hydroxide, sodium carbonate, alkaline earth oxides and hydroxides, ammonia hexamethylenetetranine ("HMTA") and tertiary amines. Resoles may also form under neutral to mildly acidic conditions. Divalent metal salts, for example, will catalyze resole formation.

The phenolic compound used in the resole synthesis is preferably phenol itself but may be cresol, xylenols, alkyl substituted phenols, bisphenol A, bisphenol F. The aldehyde used in the resole synthesis is preferably formaldehyde but may be another aldehyde such as acetaldehyde, propionaldehyde, n-butyraldehyde, isobutyraldehyde, benzaldehyde, glyoxal, and furfural.

The stable aqueous solution of the present invention may also be used in the synthesis of resole derivatives. For example, the stable aqueous solution may be used in the synthesis of an alkoxy-modified-resole. U.S. Pat. No. 4,634,758. herein incorporated by reference in its entirety, discloses a process for manufacturing alkoxy-modified resoles. As another example, the stable aqueous solution of the present invention may be used in the synthesis of a resole modified with an aliphatic polyhydroxy compound. The aliphatic polyhydroxy compound is covalently bound into the resole. U.S. Pat. No. 5,189,079. herein incorporated by reference in its entirety, discloses a process for making resoles covalently bound with polyhydric alcohols.

A typical process for resole synthesis is described as follows. Reactants are introduced into a 1 liter four-necked round-bottom flask. The flask is fitted with means to stir the flask contents, means to monitor the temperature of the flask contents, and means to reflux volatile components and products. Reflux is afforded by use of a reflux condenser fitted to one opening of the four-neck flask. The condenser is typically cooled using water. Reactants are pre-weighed before addition to the four-necked flask. The stable aqueous solution of the present invention may be added at any point during the synthesis. It is well known in the art that the weights of reactants are adjusted at the time of addition to account for differences between the nominal assay and the precise assay of the reactant. The flask contents are heated by an electric heating mantle that is controlled by a rheostat, or by use of a steam table, so that specific temperatures may be reached and maintained. Other arrangements will be known to those skilled in the art.

Similar to the laboratory process described above, larger-scale batches of resoles, of course, may also be made. Conceptually, the two processes are the same. In making the larger plant-scale batches, a reactor vessel is used that possesses similar process control capability as the laboratory reaction flask. Therefore, the reactor vessel provides means for mixing reactants, means for measuring and controlling the temperature of the reactants, means for refluxing any volatile compounds in the reactor vessel, and means for distilling off the volatile compounds.

The process for making resoles described above presents the basic aspects of such a process. It is understood by those of skill in the art that modifications to such a process may be made and at that various additives, in addition to the basic components described above, may be used. For the examples provided below, formaldehyde is added in what is termed in the art as a programmed addition. In such an addition, formaldehyde is metered into a flask or reactor vessel over a period of time so that a maximum temperature is not exceeded. Those of skill in the art will recognize, however, that whether the formaldehyde is added in a single charge or is added in a programmed addition will not affect the final resin product.

It has also been discovered that, surprisingly, water tolerance is one means to determine when the bisphenolic stillbottoms are to be added to a partially reacted resole, in order to produce resins that exhibit a preferred paper saturation at an appropriately low free phenol content, as discussed above. If the bisphenolic stillbottom is added at a high water tolerance, the resulting resole has a very slow cure speed. If the bisphenolic stillbottom is added at a low water tolerance, the resulting aqueous resole will not penetrate the paper.

Novolac Synthesis

Novolac resins are obtained by the reaction of a phenol and an aldehyde in a strongly acidic pH region. Suitable acid catalysts include the strong mineral acids such as sulfric acid, phosphoric acid and hydrochloric acid as well as organic acid catalysts such as oxalic acid, para toluene-sulfonic acid, and inorganic salts such as zinc acetate, or zinc borate. The phenol is preferably phenol itself but a portion of the phenol can be substituted with cresol, xylenols, alkyl substituted phenols such as ethylphenol, propylphenol, and mixtures thereof. The aldehyde is preferably formaldehyde but other aldehydes such as acetaldehyde, benzaldehyde, and furfural can also be used to partially or totally replace the formaldehyde.

The reaction of the aldehyde and phenol is carried out at a molar ratio of 1 mole of the phenol to about 0.40 to 0.85 mole of the aldehyde. For practical purposes, phenolic novolacs do not harden upon heating but remain soluble and fusible unless a hardener (curing agent) is present.

Water Tolerance Measurements

The water tolerance test determines the compatibility of the partially reacted resole with water. In this test, the amount of water which may be added to the partially reacted resole while still maintaining a homogeneous solution is determined. The results of the test are expressed in terms of a percentage of the weight of resole equal to the amount of water added.

The water tolerance test employs distilled or de-ionized water, a laboratory balance, reading to 0.01 gram, test tubes, a constant temperature bath set to 25° C., and other standard laboratory equipment that will be known to those of skill in the art. The distilled or de-ionized water is brought to 25.0±0.1° C. Approximately 10–3 grams of a resin sample is weighed into a test tube and the weight recorded. Next 10–3 grams of water is added to the test tube. The test tube is then capped and shaken to insure that sample is thoroughly mixed with water. If the test tube exhibits a cloud, the test is restarted and a lesser amount of water than first used is added to the test tube. Next the test tube is placed in the 25° C. water bath and the sample is agitated. Additional water is incrementally added until the cloud point of the sample is reached. The cloud point end point occurs when small white alphanumeric characters on a black background behind the sample can no longer be read when looking through the sample. The final total weight of the water added to the test tube is determined and recorded. The water tolerance of the sample is then calculated as the amount of water added to the sample divided by the initial sample weight.

Free Phenol Determination

The unreacted phenol content in phenolic resins may be determined using any of the well known gas chromatographic methods. In the method used in the examples below, a gas chromatograph equipped with an FID detector and a 6'×⅛" column with 1.2% Atpet-80 and 6.8% di-n-decylphthalate on 60/80 Anachrom ABS is used. The column oven temperature is maintained at about 130° C., the injection port temperature at about 220° C., and the detector temperature at about 220° C. Those of ordinary skill in the art will recognize variations of these components and parameters that may be used. Resin samples are dissolved in a suitable solvent and spiked with p-cresol as a standard. After mixing, the solution of resin, solvent and standard are injected into the gas chromatograph and the areas under the phenol and p-cresol peaks are integrated. The concentration of the free phenol may then be calculated.

Refractive Index Determination

The refractive index of resin samples was determined using the well-known Abbe refractometer. Measurements were made at 25° C., with the prisms of the refractometer maintained at this temperature by a circulating constant temperature bath.

Resole Viscosity Determination

Resole viscosity was determined using the well-known Brookfield viscometer. The Brookfield viscometer measures the viscous resistance to a rotating spindle immersed in a fluid. The torque necessary to rotate the spindle in the fluid is expressed in centipoise. For the results provided below, a Brookfield Digital Viscometer Model DV-II+ was used. Viscosities were determined at a temperature of 25° C. and the Brookfield Viscometer was maintained at about this temperature using a circulating constant temperature bath.

Gel Time Determination

The gel time of a liquid resin is the length of time, typically expressed in minutes, required for a resin to become infusible at a given standard temperature. For this test, a Sunshine Gel Time Meter, catalog number 22. available from Sunshine Scientific Instrument Inc., Philadelphia, Pa., is used to measure the end point of the gel time. In this method, a constant boiling temperature solvent is used. For gel time measurements reported below, tetrachloroethylene (perchloroethylene) was used, which has a constant boiling temperature of 121° C. Accordingly, the gel times reported below were determined at 121° C. The Sunshine Gel Time Meter will automatically identify the end point of the gel time.

Resole Synthesis

EXAMPLE 3

To a flask, as described earlier, 100 parts of phenol, 3.5 parts of 50% aqueous 50% sodium hydroxide, 1 part of sodium sulfite, and 14.9 parts of V-390 were added. These components were heated to about 65C., under mixing and atmospheric pressure. Next, 111 parts of aqueous 50% formaldehyde solution was metered into the flask over a 50 minute period. The temperature of these component reactants was held at about 70C. and allowed to react under mixing for about 120 minutes. The volatile contents of the flask were then distilled off under vacuum of about 22 inches Hg until a distillate weight of 21.65 Parts was attained. The contents of the flask were then held at 65C. until a free phenol of about 6.0% was attained. The contents of the flask were cooled to 25C. and 2.5 parts of acetic acid was added. The pH was then adjusted to 6.56 with a small amount of 50% sodium hydroxide.

The resin thus prepared had a refractive index of 1.5409, a free phenol content of 5.6%, and a viscosity of 433 cps.

Resole Synthesis Using Bisphenolic Stillbottoms

EXAMPLE 4

To a flask, as described above, 100 parts of phenol, 3.5 parts of a 50% aqueous solution of sodium hydroxide, 1 part of sodium sulfite, and 14.9 parts of V-390 were added. These components were heated to about 65° C., under mixing and atmospheric pressure. Next, 111 parts of a 50% aqueous formaldehyde solution was metered into the flask over a 50 minute period. The temperature of these component reactants were held at about 70° C. and allowed to react under mixing and reflux for about 120 minutes. The volatile contents of the flask were then distilled off under a vacuum of about 22 inches Hg to a distillate weight of 32.1 parts A residual free formaldehyde content of about 1% was attained. The contents of the flask was cooled to about 25° C. and 2.75 parts of acetic acid and 6 parts of water was added.

The resin thus prepared had a refractive index of 1.5405, a free phenol content of 7.8%, and a viscosity of 211 centipoise. The gel time of this resin, at 121° C., was 22.9 minutes.

Resole Synthesis

EXAMPLE 5

To a reactor vessel, 100 parts of phenol, 1 part of sodium sulfite, 3.5 parts of a 50% aqueous solution of sodium hydroxide were added. These components were heated to about 65C. under mixing and atmospheric pressure. Next, 111 parts of a 50% aqueous formaldehyde solution was metered into the vessel over a 50 minute period. The temperature of these component reactants was held at about 70C. for 120 minutes. The volatile contents of the vessel were then distilled off under vacuum of 23.8 inches Hg until a distillate weight of 21.5 parts was attained. The contents of the vessel were then held at 65C. until a water tolerance of 577% was attained. The contents of the vessel were cooled to 55C. and 14.9 parts of V-390 was added. The temperature was held at 55C. for 45 minutes after the addition was completed. The contents of the vessel were cooled to about 45C. and 2.75 parts of acetic acid was added. The pH was then adjusted to 6.86 with acetic acid and the viscosity to 270 cups with water.

The resin thus prepared had a refractive index of 1.5410, a free phenol content of 5.3%, and a viscosity of 270 cups.

Resole Synthesis Using Storage Stable Aqueous Solution

EXAMPLE 6

A resole resin was prepared according to the methods of the present invention using the storage stable solution of example 2. It was discovered that when the storage stable solution was used, no significant difference in resin properties were obtained when compared to a resin prepared using neat bisphenolic stillbottoms.

To a flask, as described above, 100 parts of phenol, 3.5 parts of a 50% aqueous solution of sodium hydroxide, and 1 part of sodium sulfite were combined. and 110 parts of a 50% aqueous formaldehyde solution, was then added over a 50 minute period. The contents of the flask (the "reactants") were heated to about 70° C., under mixing and atmospheric pressure. The temperature of the reactants were held at about 70° C. and allowed to react under mixing and reflux for about 90 minutes. The volatile contents of the flask were then distilled off under a vacuum of about 25 inches Hg until a distillate weight of 25.65 parts was attained. The flask contents were then allowed to react under atmospheric pressure at 66° C. until a water tolerance of 1030% was obtained. At this point in the reaction the flask contents were cooled to about 60° C. Next, 16.55 parts of the storage stable solution of example 2 was added to the flask. The contents of the flask were then allowed to continue to mix and react for about 10 minutes at a temperature of about 60° C. At the end of the 90 minutes reaction time, the contents of the flask were rapidly cooled to about 25° C., at which point 3 parts of acetic acid was added.

The resin thus prepared had a refractive index of 1.5402. a free phenol content of 6.0%, and a viscosity of 209 centipoise. The gel time of this resin was 22.15 minutes at 121° C.

Resole Synthesis Using Bisphenolic Stillbottoms

EXAMPLE 7

To a reactor vessel, as described above, 100 parts of phenol, and 3 parts of a 50% aqueous solution of sodium hydroxide were combined and 115 parts of a 50% aqueous formaldehyde solution was then added over a 50 minute period. The contents of the reactor vessel (the "reactants") were heated to about 75° C., under mixing and a vacuum of about 20 inches of Hg, until reflux initiated. The reactants were allowed to react at 75° C. under reflux for about 1.5 hours. At the end of this 1.5 hour period, the volatile components of the flask were distilled off at a temperature of about 60° C. and a vacuum of about 20 inches of Hg, to a distilled weight of about 22.4 parts. The reactants were then held under atmospheric pressure and 65° C. until a water tolerance of 551% was obtained. At this point in the reaction, 8.5 parts of methanol. 15 parts of V-390, and 2.7 parts of urea were added to the flask. The temperature of the reactor vessel contents was reduced to about 40° C. and 1.8 parts of acetic acid were added to the reactor vessel.

The resin thus prepared was determined to have a refractive index of 1.5373, a viscosity of 191 centipoise, and a free phenol content of 5.3%. The gel time of the resin was 19.1 minutes at 121° C.

Use of a Bisphenolic Stillbottom Compared to Use of Bisphenol A

The effect of the use of a bisphenolic stillbottom to the synthesis reactants of a resole resin on the paper penetration times was further studied. This result was compared to the paper penetration properties of a resin prepared using bisphenol A. In these examples, either bisphenolic stillbottom or bisphenol A, as noted, were added with the initial charge of phenol and formaldehyde in the preparation of the resole resin.

Resole Synthesis Using Bisphenol A

EXAMPLE 8

To a flask, as described above, 100 parts of phenol, 3.5 parts of a 50% aqueous solution of sodium hydroxide, 1.0 parts of sodium sulfite and 10 parts of Bisphenol-A were added. These components were heated to about 65° C., under mixing and atmospheric pressure. Next, 111.0 parts of a 50% aqueous formaldehyde solution was metered into the flask over a 50 minute period at 70° C. The temperature of these component reactants were held at about 70° C. and allowed to react under mixing and reflux for about 2 hours. The volatile contents of the flask were then distilled off under a vacuum of about 25 inches Hg until a distillate weight of 31.9 parts and a residual free formaldehyde content of about 1% was attained. The contents of the flask was cooled to about 25° C. and 2.75 parts of acetic acid was added.

The resin thus prepared had a refractive index of 1.5400, a free phenol content of 8.3%, and a viscosity of 175 centipoise.

Resole Synthesis Using Bisphenolic Stillbottoms

EXAMPLE 9

The present example demonstrates the manufacture of the resins of the present invention on a large, commercial, scale. To a reactor vessel, as described above. 5,963.0 pounds of phenol, and 179.0 pounds of a 50% aqueous solution of sodium hydroxide were combined and 6,858.0 pounds of a 50% aqueous formaldehyde solution was then added over a 50 minute period. The contents of me reactor vessel (the "reactants") were heated to about 75° C., under mixing and a vacuum of about 20 inches of Hg, until reflux initiated. The reactants were allowed to react under reflux for about 2 hours. The temperature of the reactants were held at about 75° C. over this 2 hour period. At the end of this 2 hour period, the volatile components of the flask were distilled off at a temperature of about 60° C. and a vacuum of about 24 inches of Hg to a distillate weight of 1410 pounds. The reactants were then held at 70° C. under reflux and about 22 inches of Hg until a water tolerance of 393% was obtained. At this point in the reaction the reactor vessel contents were cooled to about 55° C. and the vacuum was maintained at about 25 inches of Hg. Next, 1151.0 pounds of V-390 was added to the reactor vessel and allowed to mix and react for about 1 hour. Next, 161.0 pounds of urea were added to the reactor vessel. The temperature of the reactor vessel contents was about 60° C., the vacuum was about 23 inches of Hg, and the reaction was continued for about 1 additional hour. At the end of this I hour reaction period 103 pounds of acetic acid were added to the reactor vessel. An additional 130 pounds of water and 12 pounds of acetic acid was added to the contents of the reactor vessel, thereby adjusting the refractive index, viscosity, and pH.

The resin thus prepared was determined to have a refractive index of 1.5435, a viscosity of 271 centipoise, and a free phenol content of 5.0%. The gel time of the resin was 18.1 minutes at 121° C.

Measuring Resin Penetration of Paper

The utility of the resins of the present invention may be determined, in part, based on the ability of the resin to penetrate paper. One parameter useful in assessing this ability is the amount time it takes the resin to penetrate paper in a standardized test.

The penetration times reported below were determined using a standardized paper penetration test. This test indicates the capability of the resin being tested to penetrate and completely wet the fibers in a paper sheet. The equipment used in the test includes: a pan capable of holding 0.5 to 1.0 inch of the resin and having a minimum diameter of 3.5 inches; a thermometer capable of reading 25.0±0.1° C.: and a stopwatch. The paper used in this test is a Westvaco 115 pound basis weight paper. The paper is cut in the shape of a 2 ¾ inch diameter circle. Prior to testing the paper is to be stored in a dessicator containing $CaCl_2 \cdot 6H_2O$ to maintain 31% R.H. (relative humidity) at 24.5° C.

To begin the test, the resin is brought to a temperature of 25° C. The paper disc is placed in the pan of resin with the "shiny" side of the paper facing the liquid resin while simultaneously starting the stopwatch. The wetting of fibers is observed as the resin penetration progresses. The time when the exposed surface area of the paper disc is initially wet through marks the end of the test. It is this time that is reported as the penetration time.

Paper Penetration Results Using Resins of Examples 3–9

The following Table 5 summarizes the results of paper saturation tests performed using the resole resins of the examples. As demonstrated, paper penetration is dependent on the water tolerance the resin had attained at the time of addition of a bisphenolic compound.

TABLE 5

| Example Number Time | Cure Time At 121° C. (minutes) | Water Tolerance At Time of Addition (%) | Free Phenol Content (%) | Initial Penetration (seconds) |
|---|---|---|---|---|
| 3 | 17.6 | infinite | 5.6 | >180 |
| 4 | 22.9 | infinite | 7.8 | 18 |
| 5 | 20.0 | 577 | 5.3 | 42 |
| 6[1] | 22.15 | 1030 | 6.0 | 30 |
| 7[2] | 19.1 | 551 | 5.3 | 21 |
| 8 | 22.2 | infinite | 8.3 | 15 |
| 9 | 19.2 | 393 | 5.0 | 70 |

[1]The resole of example 6 was made using the storage stable solution of the present invention.
[2]The resole of example 7 was made using methanol as the solvent. All others are water based products.

As demonstrated by the data of Table 5, the stable solution of the present invention provides for the manufacture of a resin that allows excellent paper penetration without adversely affecting gel or free phenol content. Furthermore, use of the stable aqueous bisphenolic solution of the present invention allows the manufacture of resin without the addition of methanol, yet exhibiting excellent paper penetration. As seen by the results of table 3, the paper penetration time is very dependent upon when the stillbottoms are added during the resin manufacture.

Further examples of resole synthesis using an alternate source of bisphenolic stillbottom are presented below.

Resole Synthesis Using Bisphenolic Stillbottoms

EXAMPLE 10

To a flask, as described above, 100 parts of phenol and 2.93 parts of a 50% aqueous solution of sodium hydroxide were added and brought to 55° C. Next, 112.6 parts of a 50% aqueous formaldehyde solution was metered into the flask over a 50 minute period. The temperature of these component reactants were held at about 75° C. and allowed to react under mixing and reflux for about 120 minutes. The volatile contents of the flask were then distilled off under a vacuum to a distillate weight of 36 parts at 60–62° C. The contents of the flask was heated to about 72° C., with the water tolerance dropping to about 580%. The contents of the flask were then further cooled to about 60° C. and 10 parts of BPA HEAVIES was added under mixing. The contents of the flask was maintained at about 60° C., under mixing, for an additional one hour period. During this one hour hold, 10 parts of water was added to adjust the solids content. Next, 2.65 parts of urea was added and the flask contents were cooled to 40° C. Next, the flask contents were cooled to 25° C. and 1.76 parts of acetic acid was added.

The resin thus prepared had a refractive index of 1.5390, a free phenol content of 5.8%. and a viscosity of 179 centipoise. The resin thus prepared exhibited a gel time of 19.5 minutes at 121° C.

Resole Synthesis Using Storage Stable Solution

EXAMPLE 11

To a flask, as described above, 100 parts of phenol and 2.92 parts of a 50% aqueous solution of sodium hydroxide were added and brought to 55° C. Next, 111.9 parts of a 50% aqueous formaldehyde solution was metered into the flask over a 50 minute period. The temperature of these component reactants were held at about 75° C. and allowed to react under mixing and reflux for about 120 minutes. The volatile contents of the flask were then distilled off under a vacuum to a distillate weight of 26.9 parts at 60° C. The contents of the flask were heated to about 70° C., allowing the water tolerance to drop to about 580%. The contents of the flask were then further cooled to about 60° C. and 11.0 parts of a storage stable solution of the present invention, consisting of 90% BPA HEAVIES in aqueous solution, was added under mixing. The contents of the flask were maintained at about 55° C., under mixing, for an additional one hour period. Next, 2.63 parts of urea was added and the flask contents were cooled to 40° C. Next, the flask contents were cooled to 25° C. and 1.69 parts of acetic acid was added.

The resin thus prepared had a refractive index of 1.5396, a free phenol content of 6.4%, and a viscosity of 197 centipoise. The resin thus prepared exhibited a gel time of 18.5 minutes at 121° C.

Example 12. presented below, illustrates novolac synthesis using a bisphenolic stillbottom.

Novolac Stillbottoms Modified

EXAMPLE 12

It has also been learned that the stillbottoms modification is not to be limited in use to that of resole resins. A stillbottoms modified novolac resin has been produced in the following manner:

To a reactor vessel, 100 parts of phenol and 11.1 parts of V-390 were added. The contents of the vessel were heated to 62–68C. under agitation wherein the V-390 easily dissolved. At this temperature. 0.36 parts of oxalic acid was added. Other acids may be used (sulfuric, etc) and are known by those practiced in the art. The contents ("reactants") of the vessel were further heated to 98–100C. Next, 43.9 parts of 50% formaldehyde solution was metered into the vessel over a 60 minute period. The temperature of these component reactants were held at 100C. for 3 hours until the free formaldehyde content of the water portion was less than 0.5%. The contents of the vessel were then distilled atmospherically to 170C. Next, vacuum distillation was initiated and continued until the desired free phenol content was obtained. In this example, it was 1.56%. The resulting product made a novolac of an orange color, tack-free, clear appearance, and having a viscosity of 4880 cps (cone & plate 100 cone; 125C.). A novolac, thus prepared, is expected to have applications in Abrasives and Friction Industries where higher temperature resistance and less brittleness would contribute to the product maintaining its integrity.

A comparison of the results of Examples 4 and 8 demonstrates that the use of a bisphenolic stillbottom in the synthesis of a resole resin can result advantageously in a product that has a comparable initial penetration time when compared to a similar resin made using bisphenol A instead of the bisphenolic stillbottom. This also demonstrates a low cost alternative to the use of the alkylidenepolyphenol, bisphenol A.

The results provided in Table 4 also demonstrate the effect of adding the bisphenolic stillbottom at an effectively infinite water tolerance. The water tolerance at the time of addition of the bisphenolic stillbottom is high, because the principle reactants, phenol and formaldehyde, are in aqueous solution and resin solids have not yet been produced.

The data disclosed herein demonstrates a preferred range of water tolerance at which a bisphenolic stillbottom is added to a reacting resole resin of about 400% to about 1100%. Although it is clear from the examples that the bisphenolic stillbottoms may be added at a water tolerance in excess of 1100%, it is preferred that the residual free phenol be less than the nominally 8% demonstrated in Examples 5, 6 and 9. By comparison, Example 6, employing a storage stable solution of the present invention added at a water tolerance of 1030%, yielded a free phenol concentration of 6%. Accordingly, the preferred upper limit of water tolerance at which a bisphenolic stillbottom is added to the reacting resole resin is about 1100%. Reference to Table 5 (example 9) demonstrates that when a bisphenolic stillbottom is added to a reacting resole resin at water tolerance of about 393%, the initial penetration time of the resulting resin is slow. However, when the bisphenolic stillbottom is added at a water tolerance of about 600–1000%, the initial penetration time is greatly reduced. Therefore, the preferred lower limit of water tolerance at which a bisphenolic stillbottom is added to the reacting resole is about 400%, as shown by examples 5 and 9.

Applications of the Compositions of the Present Invention

The resins of the present invention are useful in, but not limited to, a broad range of laminating and paper preparation processes. For example, the resins of the present invention may be used in conventional laminating processes, such as used for the manufacture of kitchen countertops. The resins of the present invention may also be used in the preparation of decorative laminates. In the laminating process, as will be understood by those of ordinary skill in the art, laminate layers are bonded together using a resin. The resins of the present invention are thus useful in bonding together the laminate layers. The resins of the present invention may be used in the preparation of saturated, or partially saturated, paper products, such as filter paper. The compositions of the present invention may also be used in paper coatings, or saturating, fiberglass bindings, abrasions, friction composites, particle board, and refractories. Generally, the composition of the present invention may be used where lower emissions and/or plasticity are sought.

Each application of the resins of the present invention may require further modification of the resoles. For example, certain laminating processes, or processes used in the preparation of filter paper, may require the addition of an alcohol, such as methanol or ethanol, to the resole, to further facilitate paper penetration. However, it should be understood, that use of the stable aqueous solution of the present invention can eliminate the use of such an alcohol for some applications by virtue of the time at which it is added.

The effective amount of the resins of the present invention used in the applications in which such resins may be used will vary from application to application. However, such amounts will be readily understood by those of ordinary skill in the art. Furthermore, the methods of making laminates and paper products, as referred to herein, will also be readily understood by those of ordinary skill in the art.

Embodiments of the present invention also provide laminates made using phenolic resins which exhibit excellent finished product properties. Such paper laminates can exhibit reduced emissions during treating when compared to laminates of the prior art because, among other reasons, the elimination of alcohol from the resin formulation and a low free phenol concentration in the resole. Furthermore, improved laminates having excellent flexibility may be made according to embodiments of the present invention.

Thus it has been disclosed in embodiments and the preferred embodiment of the present invention, a storage stable solution of bisphenolic stillbottoms and solvents including water and other solvents. A method of making such stable solutions is likewise disclosed. It has also been disclosed in embodiments of the present invention resins made using such storage stable solutions. Such resins exhibit a low free phenol content and allow the production of laminates with desirable physical properties related to resin penetration of the paper. Improved laminates having excellent flexibility have also been disclosed in embodiments of the present invention. The present invention also provides a method by which paper penetration may be controlled as a function of the water tolerance and the time at which the stillbottoms are added. Other embodiments can be easily envisioned within the basic principles of the present invention.

It should be understood that various changes and modifications preferred in the embodiment described herein will be apparent to those skilled in the art. Such changes and modifications can be made without departing from the spirit and scope of the present invention and without demising the attendant advantages. It is, therefore, intended that such changes and modifications be covered by the appended claims.

What is claimed is:

1. A bisphenolic composition comprising:
   from about 99% to about 85%, based on the weight of the composition, of a bisphenolic stillbottom; and
   from about 1% to about 15%, based on the weight of the composition, of a solvent;
   wherein the bisphenolic composition is a single phase and the sum of the percentage of bisphenolic stillbottom present in the composition and the percentage of the solvent in the bisphenolic stillbottom is about 100%.

2. The solution of claim 1 wherein the bisphenolic stillbottom is present in an amount of from about 99% to about 90% and the solvent is present in an amount of from about 1% to about 10%.

3. The solution of claim 1 wherein the bisphenolic stillbottom comprises:

| | |
|---|---|
| p,p-Bisphenol A | 10%–84%; |
| o,p-Bisphenol A | 0%–30%; |
| Trisphenol | 10%–25%; |
| Chroman-I | 0%–3%; |
| Phenol | 0%–25%; and |
| Other Phenol-Acetone Reaction Products; | 45%–75% | wherein, the phenol-acetone reaction products do not include p,p-Bisphenol A, o,p-Bisphenol A, trisphenol, Chroman I, and phenol.

4. The solution of claim 1 wherein the solvent is selected from the group consisting of water, acetone, methylethylketone, isopropyl alcohol, phenol and toluene.

5. The solution of claim 4 wherein the solvent is water.

6. The solution of claim 4 wherein the solvent is a mixture of water and acetone.

7. A bisphenolic composition comprising:
   a bisphenolic stillbottom; and
   a solvent;
   wherein the bisphenolic composition is a single phase and the solvent is selected from the group consisting of water, acetone, methylethylketone, isopropyl alcohol, and phenol.

8. A method for making a stable composition of a bisphenolic stillbottom and a solvent, the method comprising the steps of:
   heating the bisphenolic stillbottom to a temperature of from about 65° C. to about 170° C.;
   adding the solvent to the heated bisphenolic stillbottom; and
   mixing the solvent and the bisphenolic stillbottom for a period of time sufficient for the solvent and the bisphenolic stillbottom to form a single-phase composition.

9. The method of claim 8 wherein the bisphenolic stillbottom is heated to a temperature of from about 120° C. to about 150° C.

10. The method of claim 8 wherein the bisphenolic stillbottom and the solvent are mixed for about 30 minutes to about 60 minutes.

11. The method of claim 8 further comprising refluxing the solvent.

12. The method of claim 8 wherein the temperature of the solvent at the time the solvent is added to the bisphenolic stillbottom is from about 25° C. to about 40° C.

13. The method of claim 8 wherein the solvent is selected from the group consisting of water, acetone, methylethylketone, isopropyl alcohol, phenol and toluene.

14. The method of claim 13 wherein the solvent is water.

15. The method of claim 13 wherein the solvent is a mixture of water and acetone.

16. A method for making a stable composition of a bisphenolic stillbottom and a solvent, the method comprising the steps of:
   heating the bisphenolic stillbottom to a temperature of from about 65° C. to about 170° C.;
   metering the solvent into the bisphenolic stillbottom over a period of time ranging from about 5 minutes to about 60 minutes while mixing the bisphenolic stillbottom; and
   mixing the bisphenolic stillbottom and the solvent for a period of time ranging from about 5 minutes to about 30 minutes.

17. The method of claim 16 wherein the bisphenolic stillbottom is heated to a temperature of from about 120° C. to about 150° C.

18. The method of claim 16 further comprising refluxing the solvent.

19. The method of claim 16 wherein the temperature of the solvent at the time the solvent is added to the bisphenolic stillbottom is from about 25° C. to about 40° C.

20. The method of claim 16 wherein the solvent is selected from the group consisting of water, acetone, methylethylketone, isopropyl alcohol, phenol and toluene.

21. The method of claim 20 wherein the solvent is water.

22. The method of claim 20 wherein the solvent is a mixture of water and acetone.

23. The product of mixing:
   a bisphenolic stillbottom having a temperature of from about 65° C. to about 170° C.; and
   a solvent;
   wherein the product is a single-phase composition.

24. The product of claim 23 wherein the bisphenolic stillbottom has a temperature of from about 120° C. to about 150° C.

25. The product of claim 23 wherein the solvent is selected from the group consisting of water, acetone, methylethylketone, isopropyl alcohol, phenol and toluene.

26. The product of claim 25 wherein the solvent is water.

27. The product of claim 25 wherein the solvent is a mixture of water and acetone.

28. A resin comprising:
a condensate of a phenolic compound, an aldehyde and a single-phase composition of a bisphenolic stillbottom and a solvent.

29. The resin of claim 28 wherein the phenolic compound is selected from the group consisting of phenol, cresol, xylenol, alkyl substituted phenol, bisphenol A, bisphenol F, and combinations thereof.

30. The resin of claim 28 wherein the aldehyde is selected from the group consisting of formaldehyde, acetaldehyde, propionaldehyde, n-butryaldehyde, isobutyraldehyde, benzaldehyde, glyoxal, furfural, and combinations thereof.

31. The resin of claim 28 wherein the single-phase composition comprises:
an amount of the bisphenolic stillbottom of from about 99% to about 85% based on the weight of the solution; and
an amount of the solvent of from about 1% to about 15% based on the weight of the solution.

32. The resin of claim 28 further comprising an alcohol.

33. The resin of claim 28 wherein the solvent is selected from the group consisting of water, acetone, methylethylketone, isopropyl alcohol, and toluene.

34. The resin of claim 33 wherein the solvent is water.

35. The resin of claim 33 wherein the solvent is a mixture of water and acetone.

36. A resin comprising the product of mixing and reacting:
a phenolic compound;
an aldehyde; and
a single-phase composition of a bisphenolic stillbottom and a solvent.

37. The resin of claim 36 wherein the phenolic compound is selected from the group consisting of phenol, cresol, xylenol, alkyl substituted phenol, bisphenol A, bisphenol F, and combinations thereof.

38. The resin of claim 36 wherein the aldehyde is selected from the group consisting of formaldehyde, acetaldehyde, propionaldehyde, n-butryaldehyde, isobutyraldehyde, benzaldehyde, glyoxal, furfural, and combinations thereof.

39. The resin of claim 36 wherein the single-phase composition comprises:
an amount of the bisphenolic stillbottom of from about 99% to about 85% based on the weight of the solution; and
an amount of the solvent of from about 1% to about 15% based on the weight of the solution.

40. The resin of claim 39 wherein the single-phase composition comprises:
an amount of bisphenolic stillbottom of from about 99% to about 90%; and
an amount of the solvent of from about 1% to about 10%.

41. The resin of claim 36 wherein the solvent is selected from the group consisting of water, acetone, methylethylketone, isopropyl alcohol, phenol and toluene.

42. The resin of claim 41 wherein the solvent is water.

43. The resin of claim 41 wherein the solvent is a mixture of water and acetone.

44. A method of making a resin, the method comprising:
mixing and reacting a phenolic compound, an aldehyde, and a resole catalyst to produce a reaction product;
determining a water tolerance of the reaction product;
adding a bisphenolic compound to the reaction product when the water tolerance is from about 400% to about 1100%; and
mixing and reacting the reaction product and the bisphenolic compound.

45. The method of claim 44 wherein the phenolic compound is selected from the group consisting of phenol, cresol, xylenol, alkyl substituted phenol, bisphenol A, bisphenol F, and combinations thereof.

46. The method of claim 44 wherein the aldehyde is selected from the group consisting of formaldehyde acetaldehyde, propionaldehyde, n-butryaldehyde, isobutyraldehyde, benzaldehyde, glyoxal, furfural, arid combinations thereof.

47. The method of claim 44 wherein the resole catalyst is selected from the group consisting of sodium hydroxide, sodium carbonate, alkaline earth oxides, alkaline earth hydroxides, ammonia, HMTA, and tertiary amines.

48. The method of claim 44 wherein the resole catalyst is a divalent metal salt.

49. The method of claim 44 wherein the bisphenolic compound is a bisphenolic stillbottom.

50. The method of claim 44 wherein the bisphenolic compound is bisphenol A.

51. The method of claim 44 wherein the bisphenolic compound is bisphenol F.

52. The method of claim 44 wherein the bisphenolic compound is a single-phase composition of bisphenolic stillbottom and a solvent.

53. The method of claim 52 wherein the single-phase composition comprises an amount of the bisphenolic stillbottom of from about 99% to about 85% based on the weight of the solution; and an amount of the solvent of from about 1% to about 15% based on the weight of the solution.

54. A method of making a resin, the method comprising:
mixing and reacting a phenolic compound, an aldehyde, a bisphenolic stillbottom and a novolac catalyst to produce a reaction product.

55. The method of claim 54 wherein the bisphenolic compound is a single-phase composition of bisphenolic stillbottom and a solvent.

56. The method of claim 54 wherein the single-phase composition comprises an amount of the bisphenolic stillbottom of from about 99% to about 85% based on the weight of the solution; and an amount of the water of from about 1% to about 15% based on the weight of the solution.

57. A resin comprising the product of mixing and reacting:
a reaction product comprising the product of mixing and reacting a phenolic compound, an aldehyde, and a resole catalyst, the reaction product having a water tolerance of from about 400% to about 1100%; and
a bisphenolic compound.

58. The resin of claim 57 wherein the phenolic compound is selected from the group consisting of phenol, cresol, xylenol, alkyl substituted phenol, bisphenol A, bisphenol F, bisphenolic stillbottoms, and combinations thereof.

59. The resin of claim 57 wherein the bisphenolic compound is a bisphenolic stillbottom.

60. The resin of claim 57 wherein the bisphenolic compound is a single-phase composition of bisphenolic stillbottom and a solvent.

61. The resin of claim 57 wherein the single-phase composition comprises an amount of the bisphenolic stillbottom of from about 99% to about 85% based on the weight of the solution; and an amount of the solvent of from about 1% to about 15% based on the weight of the solution.

62. A resin impregnated product comprising:
   a substrate; and
   an effective amount of the resin of claim 28;
   wherein the substrate is impregnated with the resin.

63. A resin impregnated product comprising:
   a substrate; and
   an effective amount of the resin of claim 32;
   wherein the substrate is impregnated with the resin.

64. A resin impregnated product comprising:
   a substrate; and
   an effective amount of the resin of claim 36;
   wherein the substrate is impregnated with the resin.

* * * * *